Figure 1:
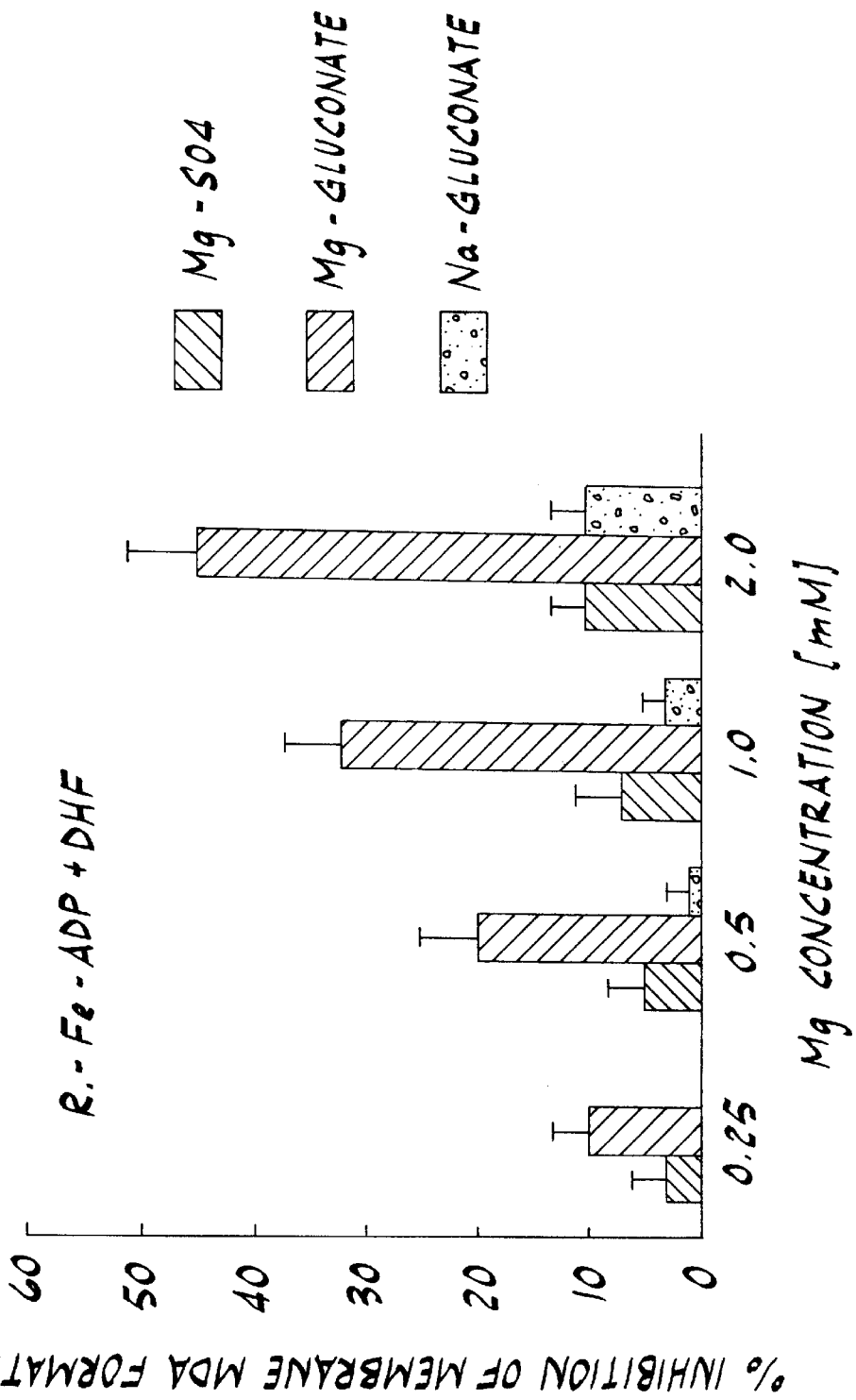

United States Patent [19]
Fleming et al.

[11] Patent Number: 5,939,394
[45] Date of Patent: Aug. 17, 1999

[54] METHODS AND COMPOSITIONS FOR THE PREVENTION AND TREATMENT OF IMMUNOLOGICAL DISORDERS, INFLAMMATORY DISEASES AND INFECTIONS

[75] Inventors: Thomas E. Fleming, St. Louis, Mo.; Herbert C. Mansmann, Jr., Newton Square, Pa.

[73] Assignee: Fleming & Company, Fenton, Mo.

[21] Appl. No.: 08/844,909

[22] Filed: Apr. 23, 1997

Related U.S. Application Data

[63] Continuation-in-part of application No. 08/588,564, Jan. 18, 1996.

[51] Int. Cl.$^6$ .......................... A61K 31/70; A61K 31/355; C07H 23/00
[52] U.S. Cl. ............................ 514/23; 514/458; 514/826; 514/855; 514/885; 514/921; 536/121
[58] Field of Search ............................ 514/23, 921, 885, 514/826, 855, 458; 536/121

[56] References Cited

U.S. PATENT DOCUMENTS

| | | | |
|---|---|---|---|
| 5,002,780 | 3/1991 | Bakta et al. ............................. | 426/72 |
| 5,260,279 | 11/1993 | Greenberg ................................ | 514/21 |
| 5,504,072 | 4/1996 | Schmidt et al. .......................... | 514/21 |
| 5,550,166 | 8/1996 | Ostlund et al. .......................... | 514/715 |

OTHER PUBLICATIONS

Kumar A. and Busse, W.W., 1995, *Scientific Am. Science & Med.*, Mar./Apr., 38–47.

Mak, I.T. et al, 1990, *Biochem. Pharm.* 40: 2169–2175.

Mak, I.T. et al, 1995, *Biochem. Pharmacol.* 50: 1531–1534.

Mak, I.T. & Weglicki, W.B., 1994, *Method Enzymol.* 234: 602–630.

Pao, E.M., Mickle, S.J., 1981, *Food Technol.* 35: 58–69.

Sheagren, J.N., 1981, *N. Engl J. Med.*, 305: 456.

Smith, L.M. and S.O. Their, eds., Pathophysiology—The Biological Principles of Disease, W.B. Saunders Company (1985) 164–172.

Verma, X. et al, 1992, *Canadian J. Neurol. Sci.* 19: 360–375.

Weitzman, S.A. and Gordon, L.J., 1990, *Blood* 76: 655.

Wiesenhutter, X. et al., 1994, *J. Rheumatol.* 21: 804–812.

Mansmann, Jr., H.C., "Consider Magnesium Homeostasis" *Pediatric Asthma, Allergy & Immunology*, 5, pp. 273–279 (1991).

Physicians' Desk Reference, 50th Edition (1996) p. 1005, "Magonate Tablets, Magonate Liquid".

*Primary Examiner*—Douglas W. Robinson
*Assistant Examiner*—Everett White
*Attorney, Agent, or Firm*—Senniger, Powers, Leavitt & Roedel

[57] ABSTRACT

The present invention relates to compositions and methods for the prevention and/or treatment of allergic, autoimmune, septic shock or infectious diseases using magnesium gluconate alone or in combination with one or more antioxidants or an antiinflammatory agent. The invention also relates to the inhibition of production of inappropriate levels of lipid mediators and cytokines.

22 Claims, 4 Drawing Sheets

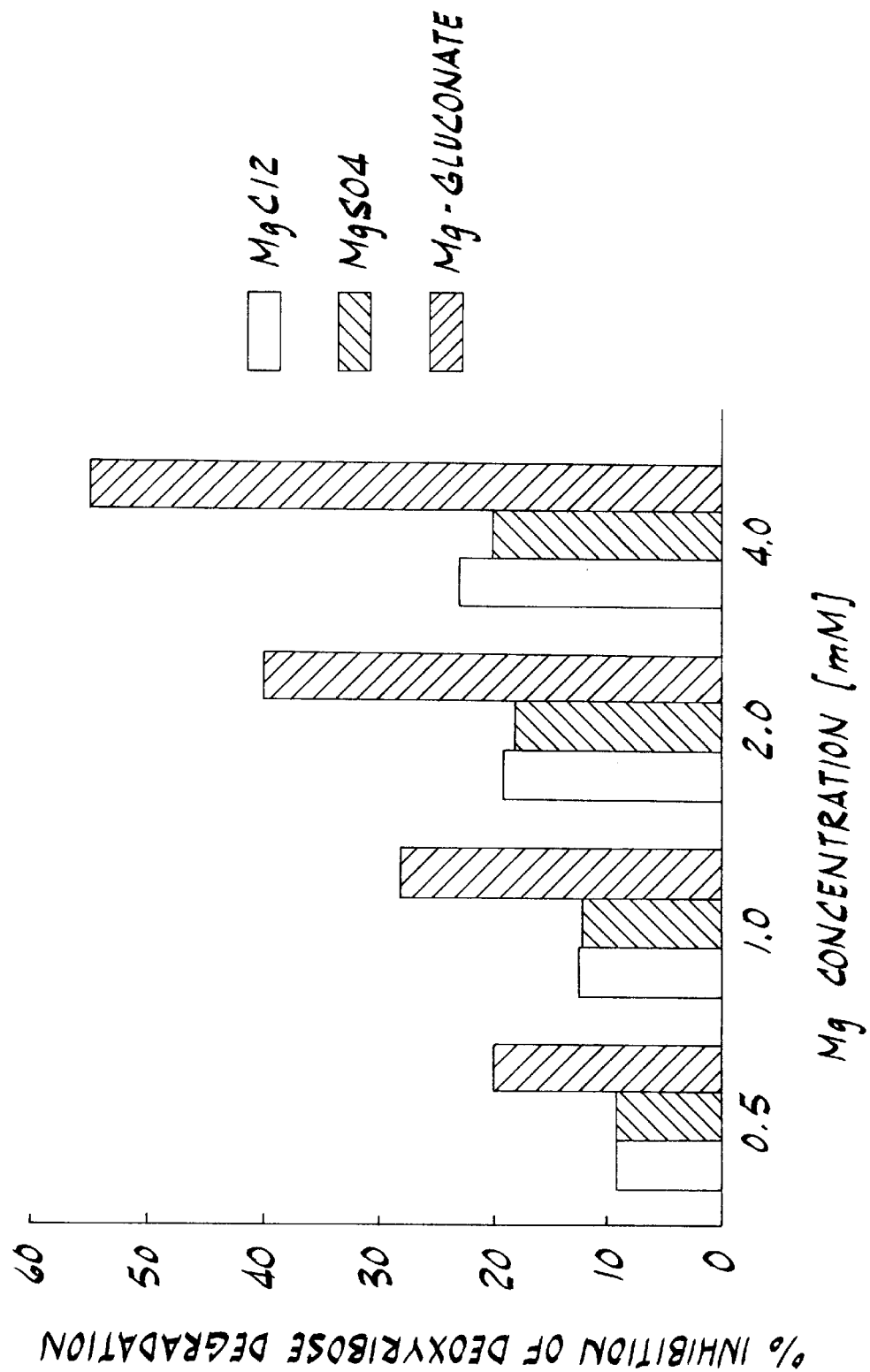

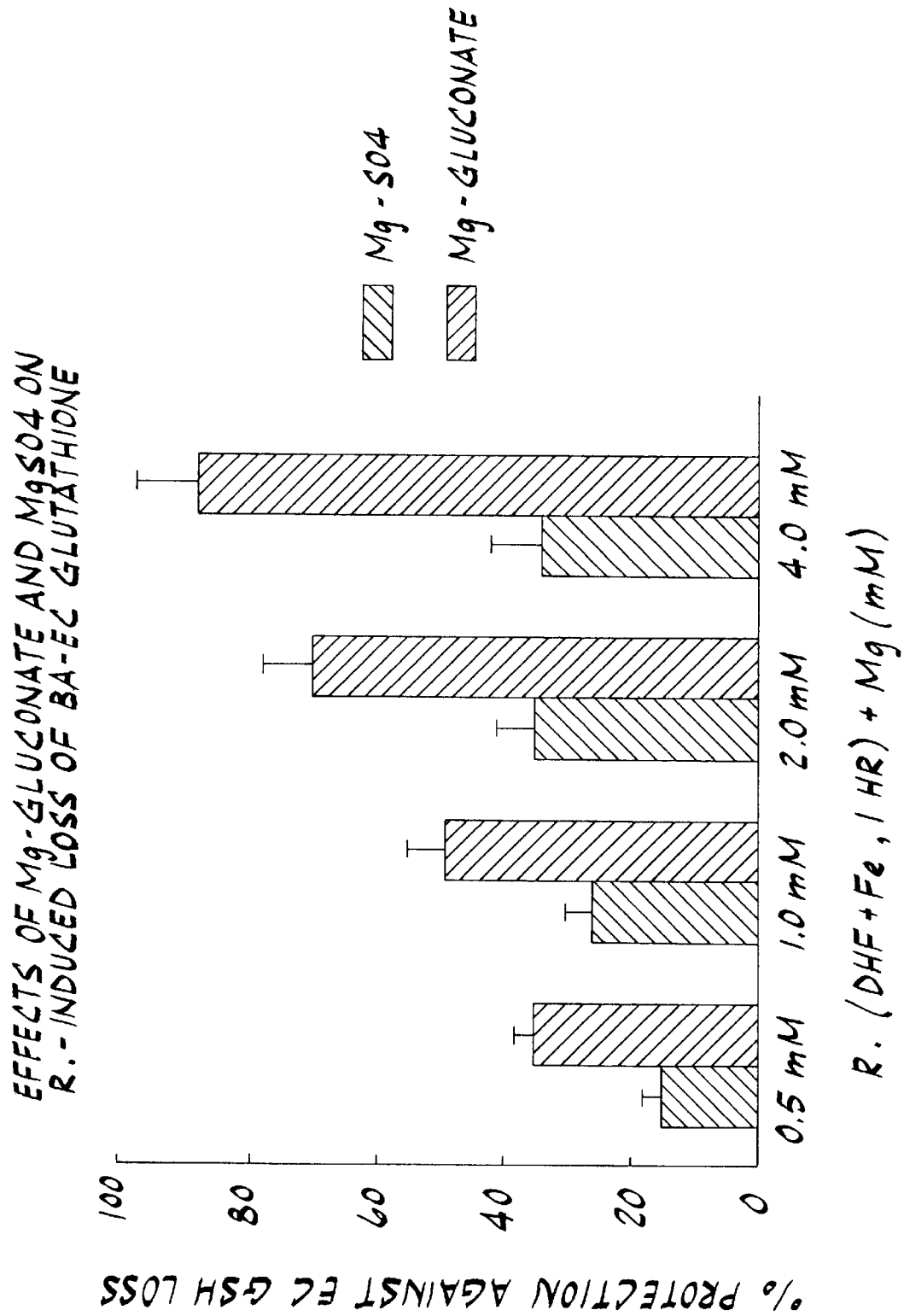

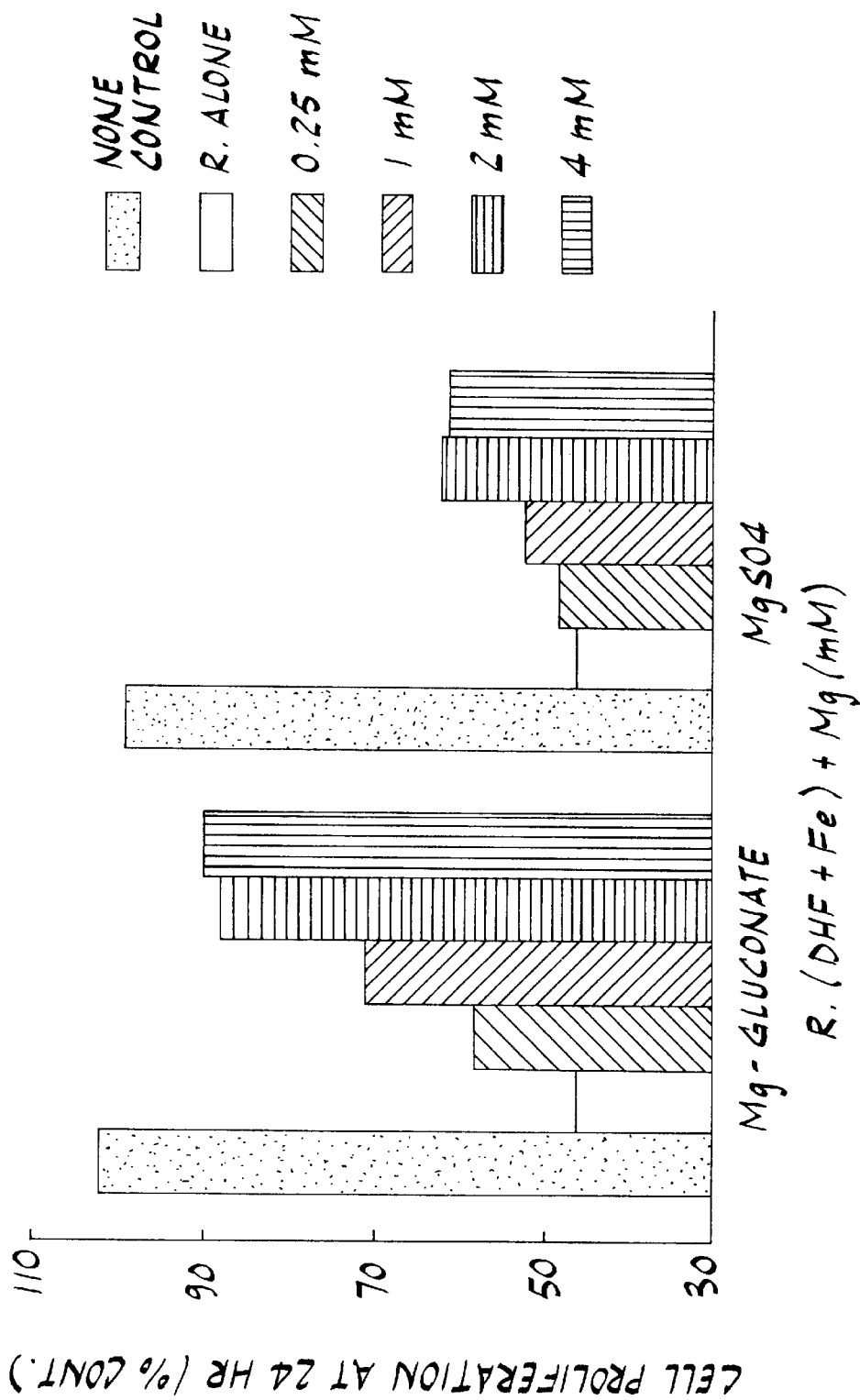

ns to environmental antigens, the
METHODS AND COMPOSITIONS FOR THE PREVENTION AND TREATMENT OF IMMUNOLOGICAL DISORDERS, INFLAMMATORY DISEASES AND INFECTIONS The present application is a Continuation-in-Part of application Ser. No. 08/588,564 filed Jan. 18, 1996, which is incorporated by reference herein in its entirety.

1. INTRODUCTION

The present invention relates to methods and compositions for the prevention and treatment of immunological disorders, inflammatory diseases, septic shock and chronic infections involving lipid peroxide- and cytokine-mediated pathology. The methods and compositions of the invention, especially suited for parenteral, enteral or topical administration prevent or inhibit oxidant-induced or cytokine mediated tissue damage, chronic inflammation and other deleterious consequences of reactive species of oxidants.

2. BACKGROUND OF THE INVENTION

The normal function of the immune system is essential for health, and dysfunction of the immune system leads to myriad diseases. For example, deficiency of immune cell production or defective immune cell function can lead to a wide spectrum of immunodeficiency diseases, and overactivity of various components of the immune system leads to the development of allergic or autoimmune diseases.

Four major components of the immune system participate in host defense and in pathogenesis of autoimmune diseases: 1) humoral immunity involving B cells, 2) cell-mediated immunity involving T cells and monocytes, 3) phagocytic cells of the reticuloendothelial system involving macrophages and polymorpho leukocytes, and 4) complement. Defects in antibody production generally result in recurrent bacterial infections. Defects in cellular immunity result in viral, mycobacterial and fungal infections, an extreme example being acquired immunodeficiency syndrome (AIDS). Disorders of phagocyte function are manifested by recurrent skin infections and deficiencies of early and late complement components are associated with autoimmune phenomena.

Sepsis is a response to infection caused by any class of microorganism including, but not limited to gram-negative and gram-positive bacteria, fungi, mycobacteria, viruses or protozoans. As sepsis progresses to septic shock, the risk of dying increases substantially. Sepsis results from complex interactions among microbial molecules, leukocytes, humoral factors, the vascular endothelial cytokines, and thromboxanes.

Current therapies for allergic, autoimmune and inflammatory diseases involve the use of nonspecific immune-modulating or immunosuppressive agents, for example, glucocorticoids or cytotoxic drugs. The goal of development of new treatments for immune-mediated diseases is to design ways to specifically interrupt pathologic immune responses, leaving nonpathologic immune responses intact. For example, the burst of reactive oxidants $\cdot O_2^-$, $H_2O_2$, $OCl^-$ and NO from white blood cells in response to bacterial and virus infections is of immediate survival value, but these oxidants have deleterious consequences in damaging DNA and leading to hyperproliferation. Weitzman, S. A. and Gordon, L. J., 1990, *Blood* 76: 655.

2.1 Allergic Diseases

The immune response in allergic diseases involves antigen recognition, humoral and cellular effector mechanisms and inflammatory reactions to environmental antigens, the inflammatory reactions being responsible in causing the deleterious effects. Some examples of allergic diseases are asthma, allergic rhinitis, eczema, atopic dermatitis and allergic contact dermatitis.

2.2 Autoimmune Diseases

Autoimmune disease is characterized by production of either antibodies that react with host tissue or immune effector T cells that are autoreactive to endogenous self peptides. Some examples of autoimmune disorders are rheumatoid arthritis, systemic lupus erythematosus, Graves' disease, immune thrombocytopenic purpura, myasthenia gravis, ulcerative colitis, Crohn's disease, scleroderma and psoriasis.

Traditionally, the main approach of treating autoimmune diseases consisted of compounds which were designed to suppress the immune system. Verma, X. et. al., 1992, *Canadian J. Neurol. Sci.* 19: 360–375. These compounds include steroids, cyclophosphamide, azathioprine and antithymocyte globulin. Another treatment modality that has been used is therapeutic plasma exchange which consists of extracting the patient's blood, separating the plasma, and replacing it with donor plasma or plasma constituents. For some patients, protein A may be useful in treating autoimmune diseases. Wiesenhutter, X. et. al., 1994, *J. Rheumatol.* 21: 804–812.

2.3 Septic Shock

Septic shock or endotoxin shock is a pathophysiologic phenomenon resulting from the release of endotoxin from gram-negative organisms. Endotoxins are lipopolysaccharide protein lipid complexes which are released from cell membranes of killed bacteria. The most common are *Escherichia coli, Aerobacter aerogenis, Proteus mirabilis, Proteus vulgaris, Pseudomonas aeroginosa*, Proteus species, Pseudomonas species, Bacteroides species and Salmonella species. The underlying pathophysiological process of septic or endotoxin shock appears to have an immunological basis involving the release of vasoactive substances and neurohumoral agents, and precipitation of coagulation abnormalities.

Treatment of septic shock is directed primarily toward establishing a specific microbial diagnosis and an entry site for the responsible microorganisms. Therapy involves use of antibiotics, glucocorticoids and necessary surgical intervention to drain abscesses or to remove infected foreign bodies. Sheagren, J. N., 1981, *N. Engl. J. Med.*, 305: 456; and Pathophysiology—The Biological Principles of Disease, ed. L. M. Smith and S. O. Thier, W. B. Saunders Company (1985) 164–172.

2.4 Magnesium

Magnesium is an important element for health and disease. It is primarily found within the cell, where it is a cofactor for over 300 enzymatic reactions in energy metabolism, and protein and nucleic acid synthesis. Magnesium deficiency may cause weakness, tremors, seizures, cardiac arrhythmias, hypokalemia, and hypocalcemia. The causes of hypomagnesemia are reduced intake, for example, poor nutrition or intravenous fluids without magnesium; reduced absorption, for example, chronic diarrhea, malabsorption, or bypass/resection of bowel; redistribution, for example, exchange transfusion or acute pancreatitis; and increased excretion, for example, medication, alcoholism, renal tubular disorders, hypercalcemia, hyperthyroidism, aldosteronism, stress or excessive lactation. A large segment of the U.S. population may have an inadequate intake of magnesium and may have a chronic latent magnesium deficiency. The ideal intake of magnesium for an adult is 15 to 20 mmol/d (36 to 48 mg/d). Magnesium is absorbed primarily in the jejunum and ileum, and healthy persons absorb about 30 to 40 percent of ingested magnesium. The majority of adults have a dietary intake of magnesium less than the recommended dietary intake (RDI) in the range of 43.3% to 93.0% of RDI. Pao, E. M., Mickle, S. J., 1981, *Food Technol*. 35: 58–69.

3. SUMMARY OF THE INVENTION

The present invention relates to methods and compositions for the prevention and treatment of immunological disorders, inflammatory diseases, septic shock and chronic infections, with an effective amount of magnesium gluconate. As used herein, immunological disorders include allergic and autoimmune diseases. As used herein, chronic infections include bacterial, viral, mycobacterial, protozoan and fungal infections.

The present invention is also directed to a method for the prevention and/or treatment of immunological disorders, inflammatory diseases, septic shock and chronic infections which involves using an effective amount of magnesium gluconate along with conventional therapy.

The present invention further relates to methods and compositions containing magnesium gluconate in combination with antioxidants, including, but not limited to, vitamin E, selenium, glutathione, glutathione isopropyl ester, or N-acetylcysteine, for use in the prevention and/or treatment of immunological disorders, inflammatory diseases, septic shock and chronic infections.

4. DESCRIPTION OF THE FIGURES

FIG. 1. Effects of magnesium gluconate on formation of lipid peroxides in endothelial cell membranes.

FIG. 2. Effects of magnesium gluconate on site-specific OH·-mediated deoxyribose oxidation.

FIG. 3. Effect of magnesium salts on R.-induced loss of BA-endothelial cell glutathione.

FIG. 4. Effect of magnesium salts on R.-induced loss of endothelial cell proliferation.

5. DETAILED DESCRIPTION OF THE INVENTION

Methods and compositions for the prevention and treatment of immunological disorders, inflammatory diseases and chronic infections, are described. The invention provides methods and compositions for intervention with magnesium gluconate to inhibit formation of lipid peroxidation products and cytokine-mediated abnormalities to prevent and/or treat immunological disorders, inflammatory diseases and chronic infections.

"Cytokines" as used herein refer to soluble proteins secreted by cells of the immune system. They mediate many of the immune and inflammatory reactions and are critical for normal host defense against pathogens. However, excessive production of cytokines may result in severe pathologic tissue injury and disease. The actions of cytokines are pleiotropic (the same protein elicits multiple effects) and redundant (one set of biologic responses may be induced by more than one cytokine) and include the interleukins, (IL-1, IL-5,IL-6 and IL-8) tumor necrosis factor-$\alpha$ and interferon-$\gamma$.

The method of the invention involves administering an effective dose of magnesium gluconate to an individual who is identified as being at enhanced risk of immunological disorders, inflammatory diseases or chronic infections and/or having an immunological disorder, inflammatory disease, septic shock or chronic infection.

It will be apparent to those skilled in the art that other magnesium salts which inhibit immunological disorders, inflammatory diseases, septic shock or chronic infections may be useful as therapeutic agents, for example, but not limited to magnesium citrate, magnesium carbonate, magnesium chloride, magnesium sulfate or magnesium stearate.

In an embodiment, the methods of the invention include administering magnesium gluconate along with traditional antiinflammatory agents, including but not limited to, glucocorticoids, non-steroidal antiinflammatory drugs, bronchodilators, $\gamma$-agonists, anticholinergic agents, antihistamines and antibiotics.

The invention provides a method of preventing and treating immunological disorders, inflammatory diseases, septic shock or chronic infections by further administering antioxidant nutrients including, but not limited to, vitamin E, selenium, glutathione, glutathione isopropyl ester, N-acetylcysteine, or mixtures thereof.

While the applicant is under no duty or obligation to explain the mechanism by which the invention works and certainly does not intend in any way for the invention to be limited to any particular mechanism of action, it may be that the ability of magnesium gluconate to prevent and inhibit abnormal production of lipid peroxides and cytokines, contributes to the efficacy or effectiveness for use in the prevention and treatment of immunological disorders, inflammatory diseases, septic shock and chronic infections. These proposed mechanisms of action are in no way meant to limit the scope of the invention and are presented purely for explanatory and/or illustrative purposes.

5.1 Allergic Diseases

Allergies account for a substantial number of human diseases with significant morbidity. The immune response in allergic diseases involves antigen recognition, humoral and cellular effector mechanisms and inflammatory reactions to allergens or environmental antigens resulting in deleterious effects. Allergic diseases have been classified into 4 types: 1) Type I—IgE antibodies fixed to mast cells react with antigens, triggering release of histamine and lipid mediators and cytokines, for example in, atopy, anaphylaxis, urticaria and angioedema; 2) Type II—IgG or IgM antibodies react with antigen on target cells and activate complement, causing cell lysis, for example in some drug reactions; 3) Type III—IgG or IgM antibodies form complexes with antigen and complement, generating neutrophil chemotactic factors with resultant local tissue inflammation, for example in serum sickness, arthus reaction and hypersensitivity lung diseases; and 4) Type IV—sensitized T lymphocytes react with antigen, producing inflammation through the action of cytokines, for example in allergic contact dermatitis.

About one out of every 10 persons in United States suffers from symptomatic atopic disease. The most common form of the disease is allergic rhinitis, usually seasonal pollen allergy (hay fever). Less frequently, atopic disease is expressed as bronchial asthma or atopic dermatitis, and rarely as gastrointestinal food allergy.

Atopic allergy is a type I hypersensitivity reaction to environmental antigens in genetically susceptible individuals who produce IgE antibodies to allergens such as pollens, molds, house dust, animal dander, or foods. Exposure to the offending allergen results in the release of mediators, including histamine, lipid mediators (Leukotrienes (LT)$B_4$ and $C_4$, prostaglandin (PG)$D_2$ and platelet-activating factor) and cytokines (IL-4, IL-5, IL-6, TNF-$\alpha$) in the target organ. The effects of these mediators on blood vessels, smooth muscle, and secretory glands, and the accompanying edema and cellular infiltrate are responsible for the clinical manifestations and pathologic features of the disease.

Asthma is a disease of the airways that is characterized by increased responsiveness of the tracheobronchial tree to a variety of stimuli. Asthma can be triggered by irritants, exercise, cold air, dust or fumes, allergens and viral infections. The response of the airways to antigen inhalation is release by the mast cells of preformed mediators (histamine, heparin, chondroitin sulfate E, tryptase and chymotryptase), cytokines (interleukin (IL)-4, IL-5, IL-6 and tumor neurosis factor (TNF)-α) and lipid mediators $LTB_4$, $LTC_4$, $PGD_2$ and platelet activating factor). The early asthmatic response takes place within minutes and is characterized by vasodilation, bronchoconstriction and mucus secretion. The late response is a complex inflammatory process mediated by leukocyte populations recruited to the airways. Kumar A. and Busse, W. W., 1995, *Scientific Am. Science & Med.*, March/April, 38–47.

5.2 Autoimmune Diseases

Autoimmune disease is characterized by production of either antibodies that react with host tissue or immune effector T cells that are autoreactive to endogenous self peptides. Three main immunopathologic mechanisms act to mediate autoimmune diseases: 1) autoantibodies are directed against functional cellular receptors and either stimulate or inhibit specialized cellular function with or without destruction of cells or tissues; 2) autoantigen—autoantibody immune complexes form in intercellular fluids or in the general circulation and ultimately mediate tissue damage; and 3) lymphocytes produce tissue lesions by release of cytokines or by attracting other destructive inflammatory cell types to the lesion. The inflammatory cell types in turn lead to production of lipid mediators and cytokines with associated inflammatory disease.

Some examples of autoimmune disorders are rheumatoid arthritis, systemic lupus erythematosus (SLE), Graves' disease, immune thrombocytopenic purpura, myasthenia gravis, Addison's disease, hemolytic anemias, neutropenias and lymphopenias.

Rheumatoid arthritis is characterized by the presence in serum of autoantibodies and immune complexes that participate in the synovitis and vasculitis by activation of complement and attraction of polymorphonuclear cells. The infiltrating polymorphonuclear cells in turn, release the inflammatory mediators such as histamine, lipid mediators and cytokines.

Other examples of disorders that may represent autoimmune phenomena include the inflammatory bowel diseases, for example, ulcerative colitis and Crohn's disease. Clinically these disorders are characterized by recurrent inflammatory involvement, humoral antibodies to colon cells and bacterial proteins and may exhibit abnormalities of cell-mediated immunity such as diminished responsiveness to various mitogenic stimuli. In addition, inflammatory mediators such as prostaglandin and thromboxane products are further stimuli for the inflammatory response.

5.3 Infectious Diseases

Infectious diseases that can be treated or prevented by the methods of the present invention are caused by infectious agents including but not limited to viruses, bacteria, fungi, protozoa and parasites.

Viral diseases that can be treated or prevented by the methods of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, human immunodeficiency virus type I (HIV-I), and human immunodeficiency virus type II (HIV-II).

Bacterial diseases that can be treated or prevented by the methods of the present invention are caused by bacteria including, but not limited to, mycobacteria rickettsia, mycoplasma, neisseria and legionella.

Protozoal diseases that can be treated or prevented by the methods of the present invention are caused by protozoa including, but not limited to, leishmania, kokzidioa, and trypanosoma.

Parasitic diseases that can be treated or prevented by the methods of the present invention are caused by parasites including, but not limited to, chlamydia and rickettsia.

5.4 Septic Shock

The microbial factors that may trigger clinical features of septic shock include the endotoxins of gram-negative bacteria. These organisms when in the bloodstream have a high propensity to cause the shock syndrome, and many features of this syndrome can be reproduced by administration of fragments of these organisms or purified preparations of the lipopolysaccharide component of their endotoxins. Gram-negative lipopolysaccharides contain three major components: an outer chain of oligosaccharide units antigenically unique to each strain of organism, a central polysaccharide core shared among different gram-negative strains and species and a proximal nonpolar lipid component known as lipid A. Lipid A can directly injure endothelial cells as well as activate macrophages to produce and release interleukin 1, plasminogen activator, lysosomal enzymes and prostaglandins, thromboxanes, leukotreines and other arachidonic acid metabolites.

Elevated levels of thromboxane $B_2$ have been documented in the circulation of some patients dying of gram-negative sepsis. In shock syndromes, thromboxane $A_2$ may participate in platelet aggregation and localized vasoconstriction in the microvasculature. Pulmonary hypertension is common in experimental models of septic shock and contrasts with the fall in systemic vascular resistance. The use of specific inhibitors of thromboxane synthetase has reduced the pulmonary vascular changes that accompany endotoxin injection into experimental animals.

5.5 Lipid Mediators

Prostaglandins, thromboxanes, leukotrienes and other arachidonic acid metabolites, for example, the hydroperoxyeicosatetraenoic acids (HPETE) and the hydroxyeicosatetraenoic acids (HETE) are important in the inflammatory and immunologic responses that the body uses to defend itself. These oxygenated metabolites are selectively produced by leukocytes, macrophages, neutrophils, eosinophils, or mast cells. There is circumstantial evidence that these substances are among the important mediators for such disorders as asthma, arthritis, adult respiratory distress syndrome, allergic rhinitis and inflammatory bowel disease. Therefore, therapeutic or preventive intervention using an agent such as magnesium gluconate which inhibits the production of such oxidants, and selectively inhibits formation of proinflammatory metabolites must result in beneficial effects.

5.6 Cytokine Mediators

Cytokines participate in all phases of immune and inflammatory responses, and some play important roles in promoting nonspecific mechanisms of host defense and inflammatory processes, for example TNF-α, IL-1, IL-5, IL-6, IL-8 and IFN-γ.

Tumor necrosis factor—x has been implicated in a variety of pathologic states in many different organs of the body. TNF-α activates blood cells and causes the adhesion of neutrophils, eosinophils, monocytes/macrophages and T and B lymphocytes. By inducing IL-6 and IL-8, TNF-α augments the chemotaxis of inflammatory cells and their penetration into tissues. Thus, TNF-α has a role in the tissue damage of allergies, autoimmune diseases and inflammatory disorders. For these reasons ways have been sought to regulate the production, secretion, or availability of active forms of TNF-α as a means to control a variety of diseases.

5.7 Choice of Magnesium Salt and Dosage

The magnesium gluconate composition of the present invention is obtained by mixing a suitable magnesium salt, for example, magnesium carbonate, with citric acid and glucono-delta-lactone. Desirably, the following concentrations are utilized: magnesium carbonate in the range of 2 mg per liter to 44 g per liter; citric acid in the range of 2.3 mg. per liter to 46.2 g per liter; and glucono-delta-lactone in the range of 6 mg per liter to an amount capable of reacting with up to 44 g per liter of magnesium carbonate and up to 46.2 g per liter of citric acid, being not greater than 130 g per liter. There results an aqueous solution of magnesium gluconate/citrate, i.e., a solution containing magnesium gluconate and magnesium citrate that exerts unexpected and stronger antioxidant, antiperoxidative and cytoprotective effects than other magnesium salts as described in Section 7.0 below.

Aqueous magnesium gluconate composition of the invention comprise formulations suitable for enteral and parenteral administration.

5.8 Pharmaceutical Preparations and Methods of Administration

Magnesium gluconate compositions for use in accordance with the present invention are formulated by mixing magnesium gluconate into an aqueous solution or by mixing a suitable magnesium salt, for example, magnesium carbonate, with glucono-delta-lactone or magnesium carbonate with glucono-delta-lactone and/or citric acid. The identified compositions that prevent and/or treat allergic diseases, autoimmune disease and infectious diseases can be administered to a patient at therapeutically effective doses. A therapeutically effective dose refers to that amount of the magnesium compound sufficient to result in the amelioration of symptoms of allergic diseases, autoimmune disease and infectious diseases. Similarly, a therapeutically effective dose refers to that amount of the antioxidants, including but not limited to, Vitamin E, selenium, glutathione, glutathione isopropyl ester or N-acetylcysteine, sufficient to result in the amelioration of symptoms of allergic diseases, autoimmune disease and infectious diseases.

Toxicity and therapeutic efficacy of the magnesium compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% in the population). The dose ratio between toxic and therapeutic effects is the therapeutic index and it can be expressed as the ratio $LD_{50}/ED_{50}$. Compounds which exhibit large therapeutic indices are preferred. The data obtained from the cell culture assays and animal studies can be used in formulating a range of dosages for use in humans.

5.9 Formulations

Magnesium gluconate compositions for use in accordance with the present invention are formulated by mixing magnesium gluconate into an aqueous solution or by mixing a suitable magnesium salt, for example, magnesium carbonate, with glucono-delta-lactone or magnesium carbonate with glucono-delta-lactone and/or citric acid. Pharmaceutical compositions for use in accordance with the present invention can be formulated by conventional means in aqueous form or by using one or more physiologically acceptable carriers, excipients or buffers.

Thus, the compounds and their physiologically acceptable salts and solvates can be formulated for administration by insufflation (either through the mouth or the nose) or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate or talc); disintegrants (e.g., potato starch or sodium starch glycolate); or wetting agents (e.g., sodium lauryl sulphate). The tablets can be coated by methods well known in the art. Liquid preparations for oral administration can take the form of, for example, aqueous solutions, syrups or suspensions, or they can be presented as a dry product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydrobenzoates, benzoates or sorbic acid). The preparations can also contain buffer salts, flavoring, coloring and sweetening agents as appropriate.

Preparations for oral administration can be formulated to give controlled release of the active compound.

For buccal administration the compositions can take the form of tablets, hard and soft gel caps or lozenges formulated in the conventional manner.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration.

Patient dosages for enteral or parenteral administration range from 10 to 150 mEq of magnesium gluconate per day, commonly 20–50 mEq per day, and typically from 20 to 30 mEq per day. Stated in terms of milligrams of Mg, usual dosages range from 100 mg per day to 1800 mg per day, preferably from 250 mg per day to 600 mg per day.

Dosage amounts of calcium for enteral administration range from 500 to 1500 mg per day. Dosage amounts of antioxidants for enteral administration range from for example for vitamin E: 200 to 100 I.U. per day. Dosage amount and interval may be adjusted to provide plasma levels which are sufficient to maintain normal metabolism and immunological response.

6. EXAMPLE
MAGNESIUM GLUCONATE INHIBITS PRODUCTION OF OXYGENATED METABOLITES

The antioxidant properties of magnesium gluconate were studied by incubating microsomal membranes prepared from endothelial cells in the presence of 0.25, 0.5, 1.0 and 2.0 mM of magnesium salts including magnesium gluconate, magnesium chloride and magnesium sulfate. Membrane malondialdehyde and site specific OH-mediated deoxyribose oxidation were measured according to methods described by Mak, I. T. & Weglicki, W. B., 1994, *Method Enzymol.* 234: 620–630; and Mak, I. T. et. al., 1990, *Biochem. Phann.* 40: 2169–2175. Results demonstrate that magnesium gluconate is more effective than magnesium chloride or magnesium sulfate in inhibiting free radical production (malondialdehyde) (FIG. 1) and in inhibiting free radical mediated deoxyribose oxidation in a dose-related manner. (FIG. 2). These data indicate magnesium gluconate has unexpected and more powerful antioxidant properties than other magnesium salts.

Cultured bovine aortic (BA) endothelial cells were incubated with R. (R.=0.83 mM dihydroxyfumarate+0.025 mM $Fe^{3+}$-ADP) for 50 mins at 37° C. Glutathione (GSH) was then determined by the enzymatic method described by Mak, I. T., et. al., 1992, *Cir. Res.* 70: 1099–1103. A loss of 56% of total GSH was observed. When the cells were pretreated for 10 mins with varying amounts of magnesium gluconate or magnesium sulfate before being exposed to R., magnesium gluconate significantly prevented the GSH loss to varying degrees (p<0.05). The EC50 was 1.1 mM (FIG. 3).

When endothelial monolayers (about 65% confluent) were incubated with R. for 30 min, the cell survival/proliferation determined by the tetrazolium salt MTT assay (Mak, I. T., et. al., 1995, *Biochem. Pharmacol.* 50: 1531–1534), decreased to 38% of control at 24 hr. Pretreatment with magnesium gluconate attenuated the loss in cell survival/proliferation (expressed as % of control (cont.)) in a dose-dependent manner compared with the cells pretreated with magnesium sulfate (FIG. 4).

It is important to note that the effects of magnesium sulfate on R.-induced loss of GSH or R.-induced loss of cell survival/proliferation were much lower than those obtained with magnesium gluconate, i.e., magnesium sulfate were approximately 33% as potent as magnesium gluconate (FIGS. 1–4).

7. EXAMPLE
TREATMENT REGIMENS FOR ACUTE, MODERATE OR SEVERE ASTHMA IN ADULTS

The invention is illustrated, by way of protocols for antiinflammatory therapy used in patients suffering from acute, moderate or severe asthma. These protocols demonstrate the effectiveness of magnesium gluconate in the treatment of various stages asthma. 30 ml Magnesium gluconate (324 mg Mg) (Magonate®—Fleming and Co., Pharmaceuticals) or in combination with methylprednisole 0.125 mg intravenous is given as per current Emergency Department Procedure. The magnesium gluconate compositions of the present invention are useful in the treatment of acute, moderate and severe asthma.

The present invention is not to be construed as limited in scope to the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A composition suitable for administration to a human subject for the prevention or treatment of allergic diseases, autoimmune diseases, septic shock or infectious diseases, said composition consisting essentially of magnesium gluconate and one or more antioxidants selected from the group consisting of vitamin E, selenium, glutathione, glutathione isopropyl ester and N-acetylcysteine.

2. The composition of claim 1, wherein the magnesium gluconate is present in solution at a concentration within the range of from about 0.1 mM to about 1.5M.

3. A method for preventing or treating allergic diseases, autoimmune diseases, septic shock or infectious diseases comprising administering to a patient a therapeutically effective amount of magnesium gluconate.

4. A method for preventing or treating allergic diseases, autoimmune diseases, septic shock or infectious diseases caused by or related to the inappropriate production of lipid mediators in a human subject comprising administering to said human subject a therapeutically effective amount of magnesium gluconate.

5. The method of claim 4, wherein the lipid mediators comprise prostaglandin $E_2$, prostaglandin $D_2$, thromboxane $B_2$, leukotriene $B_4$, leukotriene $C_4$, malondialdehyde, hydroperoxyeicosatetraenoic acids or hydroxyeicosatetraenoic acids.

6. The method of claim 4, wherein magnesium gluconate may be administered in solution at a dose range of approximately 0.1 mM to 1.5M.

7. The method of claim 4, wherein the magnesium gluconate is administered enterally.

8. The method of claim 4, wherein the magnesium gluconate is administered parenterally.

9. The method of claim 4, wherein the magnesium gluconate is administered topically or rectally.

10. The method of claim 3 or 4, wherein the allergic diseases comprise asthma, allergic rhinitis, eczema, atopic dermatitis or allergic contact dermatitis.

11. The method of claim 3 or 4, wherein the autoimmune diseases comprise rheumatoid arthritis, systemic lupus erythematosus, Graves' disease, immune thrombocytopenic purpura, myasthenia gravis, ulcerative colitis, Crohn's disease, scleroderma or psoriasis.

12. The method of claim 3 or 4, wherein the infectious diseases may be caused by pathogens comprising viruses, bacteria, fungi, protozoa or parasites.

13. A method for preventing or treating allergic diseases, autoimmune diseases, septic shock or infectious diseases caused by or related to the inappropriate production of cytokines in a human subject comprising administering to said human subject a therapeutically effective amount of magnesium gluconate.

14. The method of claim 13, wherein the cytokines comprise tumor necrosis factor-α, interleukin-1, interleukin-5, interleukin-6, interleukin-8 or interferon-γ.

15. The method of claim 13, wherein the magnesium gluconate is in solution at a dose range of approximately 0.1 mM to 1.5M.

16. The method of claim 13, wherein the magnesium gluconate is administered enterally.

17. The method of claim 13, wherein the magnesium gluconate is administered parenterally.

18. The method of claim 13, wherein the magnesium gluconate is administered topically or rectally.

19. The method of claim 13, wherein the allergic diseases comprise asthma, allergic rhinitus, eczema, atopic dermatitis or allergic contact dermatitis.

20. The method of claim 13, wherein the autoimmune diseases comprise rheumatoid arthritis, systemic lupus erythematosus, Graves' disease, immune thrombocytopenic purpura, myasthenia gravis, ulcerative colitis, Crohn's disease, scleroderma or psoriasis.

21. The method of claim 13, wherein the infectious diseases may be caused by pathogens comprising viruses, bacteria, fungi, protozoa or parasites.

22. A method for treating a human subject for septic shock caused by gram-negative organisms, selected from the group consisting of *Escherichia coli, Aerobacter aerogenis, Proteus mirabilis, Proteus vulgaris, Pseudomonas aeroginosa*, Bacteroides species and Salmonella species comprising administering to a patient having such medical condition a therapeutically effective amount of magnesium gluconate.

* * * * *